(12) United States Patent
KiliçDelice et al.

(10) Patent No.: US 11,412,997 B2
(45) Date of Patent: Aug. 16, 2022

(54) PENDANT DEVICE AND PATIENT TREATMENT AND REPORTING METHOD

(71) Applicant: ATATÜRK ÜNIVERSITESI BILIMSEL ARASTIRMA PROJELERI BIRIMI, Erzurum (AR)

(72) Inventors: Elif KiliçDelice, Erzurum (AR); Orhan Delice, Erzurum (AR); Aysegül Turan, Giresun (AR); Betül Ertas, Erzurum (AR); Zeynep Büsra Öztürk, Bayburt (AR); Memmet Sahin, Erzurum (TR)

(73) Assignee: ATATÜRK ÜNIVERSITESI BILIMSEL ARASTIRMA PROJELERI BIRIMI, Erzurm (TR)

( * ) Notice: Subject to any disclaimer, the term of this patent is extended or adjusted under 35 U.S.C. 154(b) by 0 days.

(21) Appl. No.: 17/051,879

(22) PCT Filed: Apr. 17, 2019

(86) PCT No.: PCT/TR2019/050251
§ 371 (c)(1),
(2) Date: Oct. 30, 2020

(87) PCT Pub. No.: WO2019/212447
PCT Pub. Date: Nov. 7, 2019

(65) Prior Publication Data
US 2021/0121135 A1    Apr. 29, 2021

(30) Foreign Application Priority Data
Apr. 30, 2018    (TR) .................................. 2018/06141

(51) Int. Cl.
*A61B 5/00*    (2006.01)
*A61B 50/28*    (2016.01)
(Continued)

(52) U.S. Cl.
CPC .............. *A61B 5/747* (2013.01); *A61B 5/021* (2013.01); *A61B 5/024* (2013.01); *A61B 5/08* (2013.01);
(Continued)

(58) Field of Classification Search
CPC ......... A61B 5/747; A61B 5/021; A61B 5/024; A61B 5/08; A61B 5/746; A61B 50/28;
(Continued)

(56) References Cited

U.S. PATENT DOCUMENTS

2004/0064342 A1    4/2004    Browne et al.
2021/0121135 A1*   4/2021    Kili Delice ............ A61B 5/021

FOREIGN PATENT DOCUMENTS

CN    202892318 U    4/2013
CN    107198569 A    9/2017

OTHER PUBLICATIONS

International Search Report and Written Opinion of the International Searching Authority for corresponding PCT/TR2019/050251 dated Feb. 26, 2020.

* cited by examiner

*Primary Examiner* — Omar Casillashernandez
(74) *Attorney, Agent, or Firm* — John Alumit

(57) ABSTRACT

Disclosed is a pendant device particularly used in emergency services of all hospitals, allowing health staff move more comfortably in resuscitation room, speeding up the procedure time of caring patient, providing more effective and faster production of patient reports, and a patient treatment reporting method achieved by use of the pendant device.

5 Claims, 2 Drawing Sheets

(51) Int. Cl.
  *A61B 90/30* (2016.01)
  *G16H 10/60* (2018.01)
  *A61B 5/021* (2006.01)
  *A61B 5/024* (2006.01)
  *A61B 5/08* (2006.01)

(52) U.S. Cl.
  CPC .............. *A61B 5/746* (2013.01); *A61B 50/28* (2016.02); *A61B 90/30* (2016.02); *G16H 10/60* (2018.01); *A61B 2090/308* (2016.02); *A61B 2560/0214* (2013.01)

(58) Field of Classification Search
  CPC .............. A61B 90/30; A61B 2090/308; A61B 2560/0214; A61B 50/13; G16H 10/60; G16H 40/63
  USPC ...................................... 340/573.1
  See application file for complete search history.

PENDANT DEVICE AND PATIENT TREATMENT AND REPORTING METHOD

THE RELATED ART

Invention relates to a pendant device particularly used in emergency services of all hospitals, allowing health staff moves more comfortably in resuscitation room, speeding up the procedure time of caring patient, providing more effective and faster production of patient reports, and a patient treatment reporting method achieved by use of the pendant device.

BACKGROUND OF THE INVENTION

There are numerous cable medical devices required for emergency treatment of patient in resuscitation room in emergency services. Not having the devices collectively causes chaos and occupation more than required. Medical devices are generally located on cart stands. Said Medical devices located on cart stands fall when it is attempted to intervene patient quickly and cause chaos. In addition, such devices occupy too much place on stands.

Pendants are located in resuscitation rooms in emergency services, in intensive care and operation theatres. Said pendants are the systems that can be provided near patient to provide all required services and devices connections needed for medical gas and electric installation. Current pendant designs have required stand for putting oxygen, aspirator, electric socket, movable arms and patient monitor. Portable pedant arm can be moved up and down by electrical engine and parked at desired location. However, the benefit provided from use of simple pendants having such simple installation is not at adequate level particularly in emergency services. Pendants are needed to be designed more based on needs and used more effectively.

The medicine given to patients intervened at resuscitation room and patient details are or can not noted down during intervention. Said details are kept as report manually as far as remembered by physician or nurse after intervention. While issuing report amount of medicines used during intervention can be written less or more, time information can be wrongly recorded or actual ex time can be recorded wrongly. In addition, the intervention operations can be forgotten and recorded wrongly. As a result thereof, wrongly recording patient information, medicines given to patient, check-in, check-out time or ex time may cause several problems, manually recording information on paper prevents safe storage of information.

As a result, due to above described disadvantages and inadequacy of existing solutions, it has been necessary to make development in the related art.

PURPOSE OF THE INVENTION

The invention has been developed with inspiration from existing situation and aims to eliminate the above mentioned disadvantages.

Purpose of invention is to provide installation of all Medical devices used in emergency intervention for the patient onto one single body in resuscitation room.

Another purpose of the invention is to provide more effective and accurate patient reports.

A further purpose of the invention is to provide speeding up intervention to patient.

Another purpose of the invention is to provide reduction in work load of health care personnel.

A further purpose of the invention is to provide proper working of health care personnel in terms of ergonomy.

Another purpose of the invention is enable health care personnel to act comfortably in resuscitation room.

The structural and characteristics features of the invention and all advantages will be understood better in detailed descriptions with the figures given below and with reference to the figures, and therefore, the assessment should be made taking into account the said figures and detailed explanations.

DESCRIPTION OF PART REFERENCES

Figure 1:
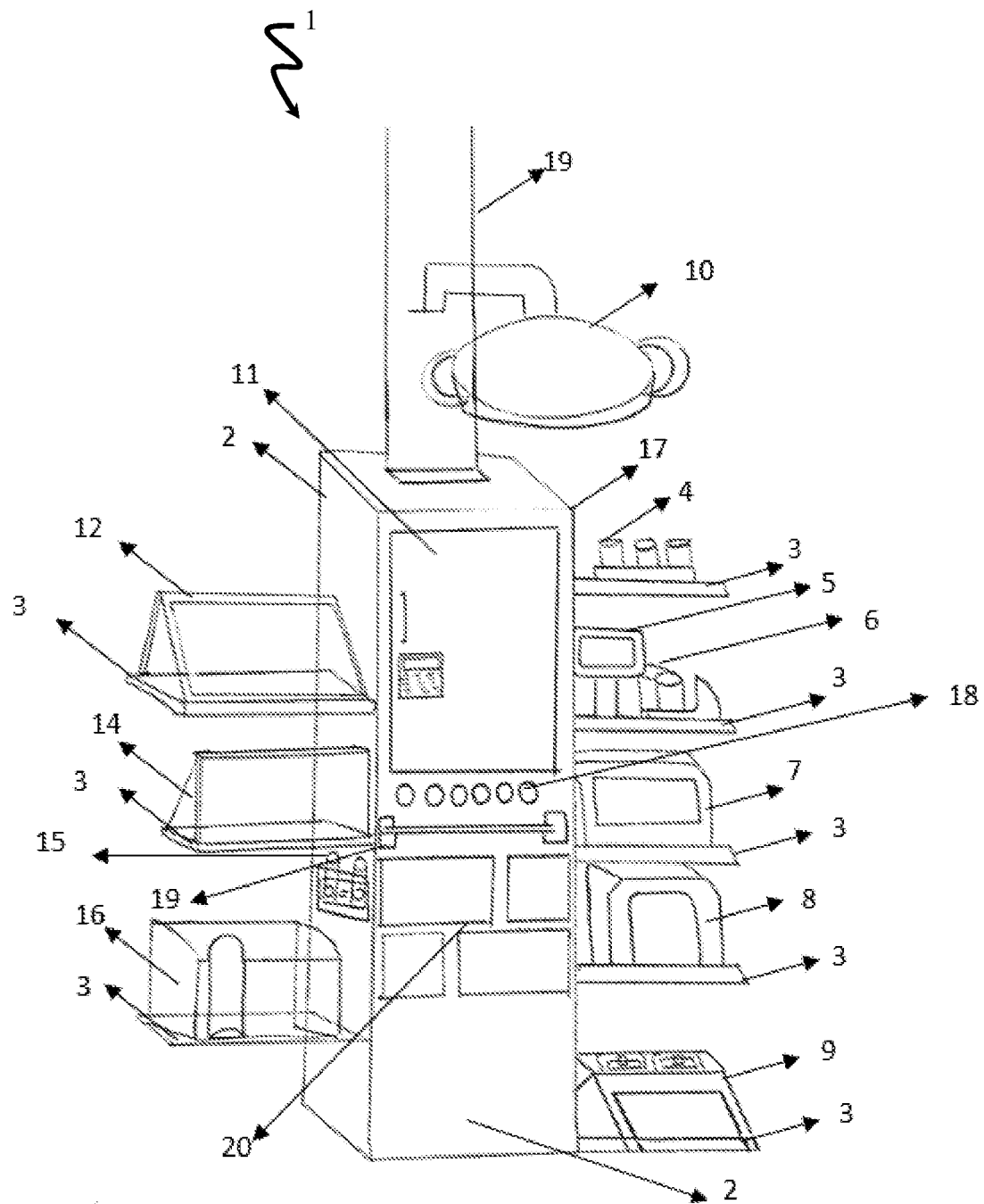
FIG. 1 is a perspective view of pendant device of the invention.

1. Pendant device
2. Body
3. Shelf
4. Aspirator device
5. Oxygen flow meter
6. Nebulizer device
7. Patient bedside monitor
8. Respiratory device
9. Defibrillator device
10. Operation lamp
11. Cooling cabin
12. Patient survey monitor
13. Patient tracking application
1301. Identity number part
1302. File number part
1303. Diagnosis selection part
1304. First name-surname part
1305. Warning message part
1306. Blood group part
1307. Age part
1308. Weight part
1309. Medical operations part
1310. Last operation part
1311. Ex part
1312. Physician-nurse part
1313. Special notes part
1314. Report production part
14. Patient tracking monitor
15. Sensor
16. Heater
17. Hanger
18. Electric socket
19. Motion mechanism
20. Medicine cabin

DETAILED DESCRIPTION OF THE INVENTION

In this detailed description, the preferred embodiments of a pendant device (1) and patient treatment and reporting method disclosed under the invention have been disclosed solely for the purpose of better understanding of the subject.

The pendant device (1) disclosed under this invention has all medical devices used in emergency intervention to patient in resuscitation room. Health care staff is enabled to access to any medical devices and medicine needed as all medical devices and medicines are placed on the pendant device (1) mounted to structural component on the ceiling, and thus faster intervention to patient is enabled. Medical devices placed on pendant device (1) and needed for treatment are approached to the patient to enable quick intervention thanks to moving structure of the pendant device (1). Pendant device (1) collects long and complex cables of medical devices and provides saving in place and thus prevents chaos that might occur during intervention.

The pendant device (1) disclosed under the invention shortens the time of intervention to patient, reduces work load of health care personnel and enables health care personnel to work comfortably ergonomically as well as their easy movement in resuscitation room.

The invention is particularly a pendant device (1) used in emergency services of all hospitals, enabling health care personnel to move more comfortably in resuscitation room, speeding up intervention to patient and providing production of patient reports more effectively and accurately and it comprises of

- at least a body (2) suspended onto ceiling, functioning as support and housing for medical devices and providing direction of cables of medical devices in a concealed way by means of paths provided therein and thus preventing cable pollution,
- More than one shelf (3) extending from said body (2) and having all medical devices used in emergency intervention of patient in resuscitation room,
- at least an aspirator device (4) located onto said shelf (3) and used in drawing fluid or particulates,
- at least an oxygen flowmeter (5) located on said shelf (3) and used to give oxygen to patient,
- at least a nebuliser device (6) located onto said shelf (3) converting medicine of fluid form into steam and providing administration thereof to patient through respiratory ways;
- at least a patient bedside monitor (7) located onto said shelf (3) and providing track of heart rhythm, blood pressure and oxygen of patient,
- at least a respiratory device (8) located onto said shelf (3) and used to provide respiration of patient when patient is not able to breath on his/her own,
- at least a defibrillator device (9) located onto said shelf (3) and giving electrical shock to provide resume of normal heart rhythm of patient when heart rhythm problem occurs,
- at least an operation lamp (10) located onto said shelf (3) and providing homogenous illumination,
- at least a cooling cabinet (11) located onto said body (2), allowing locking to provide reduction in use by health care personnel other than use of medicines such as morphine and other medicines and capable to cool and reduce medicine supply period,
- at least a patient survey monitor (12) located onto said shelf (3) and providing fast patient film and analysis examination and time of intervening to patient,
- at least a patient tracking monitor (14) located on said shelf (3) wherein at least a patient tracking application (13) is installed, which is touch screen structure, provides recording of patient information, medicine given to patient and medical treatments given to patient and reporting thereof,
- at least a sensor (15) located to said body (2), said shelf (3) or stretcher, operating through said patient tracking monitor (14) and application used therein, providing opening of record screen and recording of weight information,
- at least a heater (16) located onto said shelf (3) and used for heating patient having low body temperature,
- at least a hanger (17) located on said shelf (3) and used to hang serums,
- more than one electric sockets (18) located on said body (2) and/or said shelf (3) used to supply electric power,
- at least a carrying mechanism (19) enabling approaching said body (2) and therefore said shelf (3) to patient or leave far from patient when requested and providing the most effective use of medical device located a said shelf (3) near patient,
- at least a medicine cabin (20) mounted onto said body (2) storing medicines, serums and other similar materials and thus facilitating medicine supply during any intervention to patient and enabling nurse to work faster and more effectively, (FIG. 1).

Patient tracking application (13) has been developed for use in medical device(s) (1) provided in the pendant device disclosed under the invention. Thus all medicines given to patient, patient information, emergency check-in, checkout times are kept and problems that might occur at judicial events are eliminated. Record of medicines given to patient as well as dosage is also kept. Thus all information is recorded accurately and safely in electronic medium and when required such information can be presented in a report form and thus any problems that might arise from absent-mindedness are prevented. Moreover, report can be printed out and delivered to authorized authorities or patients whenever required. Particularly, in cases when autopsy is required, medical interventions made to the patient can be seen in detail under said report and it can be discovered if health care personnel make any mistake during treatment of patient.

Patient tracking application (13) is preferably written in Java Script (Node.js), PHP, Html and run an all operating systems in devices such as mobile phones, computers and other devices without need for any extension on web-based system. Patient tracking application (13) is closed to external intervention and is only accessible by authorised persons for reporting.

Figure 2:
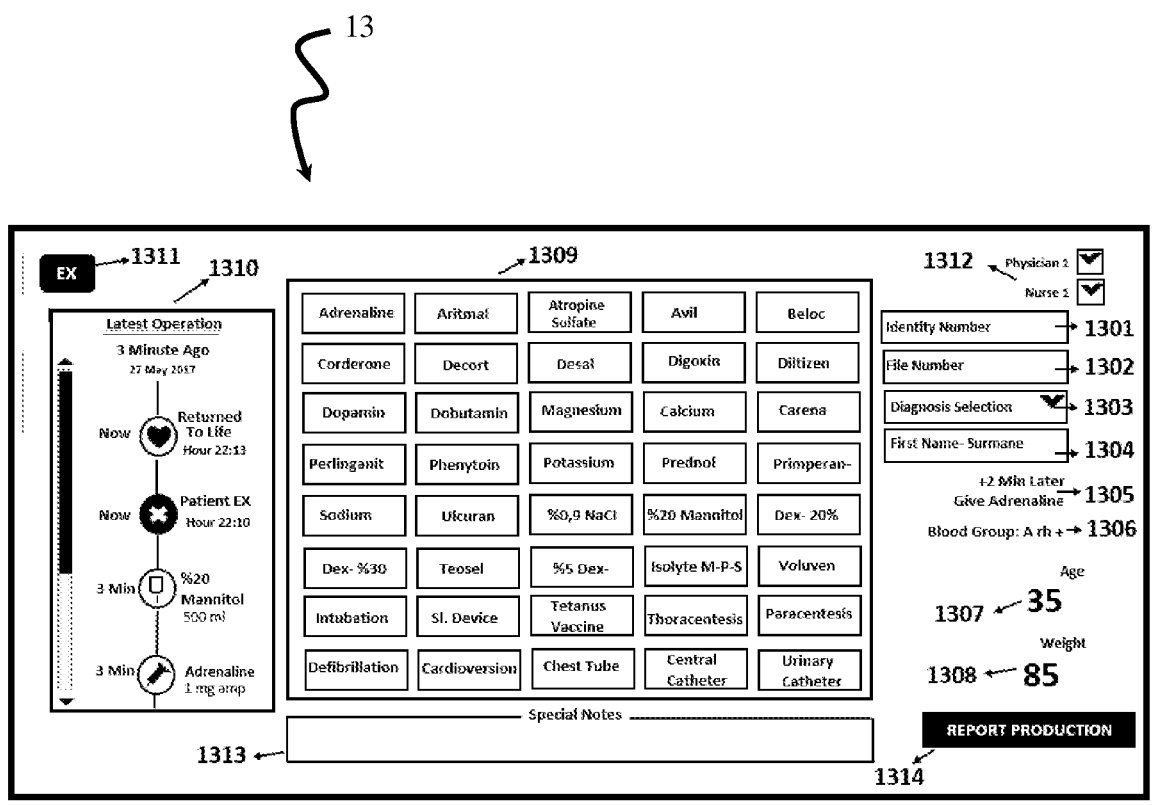
FIG. 2 is a view of sample interface of patient tracking application.

As shown in FIG. 2, patient tracking application (13) preferably has

- at least an identity (1301) part where patient's identity number is entered
- at least a file number (1302) part where patient's file number is entered
- at least a diagnosis selection part (1303) where diagnosis is selected for patient,
- at least a first name-surname part (1304) where patient's first name-surname is entered,
- at least a warning message part (1305) reminding the medicines required to be re-given to patient after a fixed time period,
- at least a blood group part (1306) where patient's blood group is entered
- at least an age part (1307) where patient's age is entered,
- at least a weight part (1308) where patient's weight is entered,
- at least a medical operations part (1309) where medical operations to be made and medicines to be given to patient are selected,
- at least a last operation part (1310) showing the latest medicine delivering operation and medical operations for patient by means of said medical operations part (1309),
- at least an Ex part (1311) where ex events are recorded, at least a physician-nurse part (1312) where physician and nurse details are recorded, at least a special notes part (1313) where special information is recorded for patient by physician, at least a report production part (1314) producing reports where all interventions to patient, emergency check-in and check-out dates and times are automatically entered and printed out.

Patient treatment and reporting method uses components provided in the pendant device (1) and the following process steps are realized by means of such components;

placement of medical devices onto shelf (3), discharge of fluids such as blood by means of aspirators (4) subject to patient's condition, feeding oxygen to patient by means of oxygen flow meter (5) when patient has lack of oxygen, giving medicine to patient through respiratory ways by concerting fluid medicine into vapour by nebulizer (6) when it is needed to give medicine by vaporization, putting respiratory device (8) if patient has no respiration, heating patient by heater (16) if temperature of patient is low, tracking patient's heart beats, blood pressure and oxygen level by means of bedside monitor (7)

adjustment of patient's arrhythmia by use of defibrillator device (9) if required, providing required illumination by use of operation lamp (10), putting on serum by means of hanger (17) if required, carrying body (2) and thus medical devices to patient by means of carrying mechanism (19)

electric power supply needed for medical devices from electric sockets (18), keeping narcotic drugs and materials in password protected cooling cabinet (11), keeping drugs, serums and other similar materials in medicine cabin (20), examination of analysis results such as x-ray, MR and tomography by patient survey monitor (12), obtaining all medical intervention made to patient, patient information, health care personnel details and reporting by patient tracking application (13) in the patient tracking monitor (14).

The process of obtaining all medical intervention made to patient, patient information, health care personnel details and reporting by patient tracking application (13) in the patient tracking monitor (14) performed in patient treatment and reporting method disclosed under the invention comprises of sub-process steps of;

creating new log in patient tracking application (13) by means of sensor (15), and entering patient emergency service check-in date and time from patient tracking application (13), entering patient identity number in identity number part (1301), getting patient details automatically from country's birth administration records by use of entered identity number or entering patient's name and surname into first name-surname part (1304) and patient's age into age part (1307), getting patient file number from hospital information management system or manually and entering patient file number in file number part (1302), measuring weight of patient by sensor (15) and entering manually or automatically into weight part (1308), getting patient blood group from hospital information management system or manually and entering it in blood group part (1306), selecting given medicines and applied medical operations to patient from medical operations part (1309) and recording automatically, reminding health care staff in reminding message part (1305) of medicines required to be given again after a certain time, display of lastly made operation to patient in latest operation part (1310) for tracking of patient, entering diagnostic decision made for patient after treatment into diagnosis selection part (1303)

recording patient ex time in Ex part (1311) in case of ex, recording name of health care staff intervening patient in physician-nurse part (1312), entering special notes of physician, if any, into special notes part (1313), use of report production part (1314) for issue of report after completion of treatment of patient and issue of report again if requested.

In pendant device (1) and patient treatment and reporting method made by use of the pendant device (1), firstly, patient is taken onto stretch as soon as s/he arrives at emergency service.

The body (2) and thus medical devices can be carried to patient by means of carrying mechanism (19) provided in pendant device (1). Said medical devices are supplied power from electric socket (18).

Medical devices located on the shelf (3) are used subject to condition of patient and treatment is started accordingly. Illumination required for treatment is provided by use of operation lamp (10).

Firstly, connection to patient bedside monitor (7) showing rhythm, oxygen and blood pressure is conducted. If patient's heart stopped, hearth massage is made by use defibrillator device (9). Fluids such as blood are removed from patient's mouth by means of aspirators (4) subject to patient's condition. If patient has no respiration, tube is connected to patient's trachea and thus connection to respiratory device (8) is provided by means of the tube. If patient suffers from asthma or copd disease, patient is put on nebuliser device (6). If patient breathes but O2 amount is low, oxygen flow meter (5) is put on and to give patient oxygen. If patient's temperature is low, heater (16) is used for heating. Medicines are given intravenously subject to cardiac rhythm of patient and respiratory condition of patient by use of medicines provided in medicine cabin (20). Medicines are injected into serum put onto hanger (17) after said treatments. If the patient is to be anesthetized and strong pain killers called narcotic drugs are needed, medicines are provided from password protected cooling cabin (11).

Patient's analysis are reviewed on survey monitor (12) Medical interventions made to patient are made by use of touch patient tracking monitor (14) where patient tracking application (13) is installed.

Log screen provided in patient tracking application (13) is automatically turned on by sensor (15) integrated to stretch and/or pendant device (1) when patient lies on the stretch. After patient's emergency service check-in date and time recording screen opens, they are automatically assigned to patient tracking application (13).

Patient's identity number is entered into identity number part (1301) on said log screen. If identity number is not entered within a time period, the log screen is preferably switched off.

Patient's name, surname and age can be entered in patient tracking application (13) manually or when patient's identity number is entered, the information is automatically taken from birth record office. Thus patient's name and surname is entered in first name-surname part (1304) and patient's age is entered in age part (1307).

Patient's file number is taken from hospital information management system and is entered into file number part (1302). In case patient has no record in hospital information management system, patient's file number is entered into file number part (1302) manually and patient's database log is obtained.

One of sensors (15) provides weighing patient. The weight value is received from sensor (15) automatically or manually transferred into weight part (1308). Thus contrary to amount of medicine given to patient on estimation by considering physical appearance of patient in today applications, amount of medicine based on patient's weight is given. Medicine dosage not given according to patient's weight increases risk of complications that patient may develop.

Patient's blood group is taken from hospital information management system and is entered into blood group part (1306). If patient is not registered in hospital information management system, patient's blood group is entered into blood group part (1306) manually.

The medicines, serum given to and operations made for patient are selected from medical operations part (1309) on screen and automatic recording of the operations is made.

Since it is required to apply adrenalin to patient having cardiopulmonary resuscitation once every 3-5 minutes, warning is given from warning message part (1305) 4 minutes after giving adrenalin in order to prevent forgetting during operation.

In the last operation part (1310), last given medicines and conducted operations are recorded in application sequence and displayed on the screen. Sliding bar is moved down and the records listed in recording time can be seen.

Diagnostic decision made for patient by physician after treatment is entered into diagnosis selection part (1303). If cases ending in ex occur, Ex part (1311) is clicked on and ex time of patient is recorded in the latest operation. First names-surnames of physician and nurse are entered in physician-nurse part (1312). Other things that physician want to indicated can be entered in special notes part (1313).

Report production part (1314) is clicked on and all conducted operations details are reported. Patient check-out date is given automatically when first report production part (1314) is pressed. When it is intended to take report information for same patient later, report production part (1314) is pressed. In such casein addition to first printed date information, the report is added the latest report production date.

The invention claimed is:

1. An apparatus for use in emergency services, the apparatus comprising:
    at least one body adapted to be suspended from above, the at least one body adapted to support and house a medical device and to support a cable of the medical device;
    a plurality of shelves extending from said at least one body;
    at least one aspirator device positioned on at least one of said plurality of shelves, said at least one aspirator device adapted to draw fluids or particulates;
    at least one oxygen flow meter positioned on at least one of said plurality of shelves and adapted to provide oxygen to a patient;
    at least one nebulizer device positioned on at least one of said plurality of shelves, said at least one nebulizer device adapted to atomize a fluid and to provide the atomized fluid to the patient through respiration;
    at least one bedside monitor positioned on at least one of said plurality of shelves, said at least one bedside monitor adapted to provide information with respect to heart rhythm and blood pressure and oxygen of the patient;
    at least one respiratory device positioned on at least one of said plurality of shelves, said at least one respiratory device adapted to provide respiration to the patient;
    at least one defibrillator device positioned on at least one of said plurality of shelves, said at least one defibrillator device adapted to provide an electrical shock to the patient;
    at least one operation lamp positioned on at least one of said plurality of shelves and adapted to provide illumination;
    at least one cooling compartment positioned on said at least one body, said at least one cooling compartment being, lockable and adapted to cool medicines positioned therein;
    at least one patient survey monitor positioned on at least one of said plurality of shelves;
    at least one patient tracking monitor positioned on at least one of said plurality of shelves, said at least one patient tracking monitor having a patient tracking mechanism installed therein, said at least one patient tracking monitor having a touch screen and being adapted to record patient information and medicine given to the patient and medical treatments given to the patient;
    at least one sensor located on said at least one body or on at least one of said plurality of shelves, said at least one sensor being cooperative with said at least one patient tracking monitor and adapted to open a record screen and to record weight information;
    at least one heater positioned on at least one of said plurality of shelves, said at least one heater adapted to heat the patient;
    at least one hanger positioned on at least one of said plurality of shelves and adapted to hang a serum bag;
    a plurality of electrical sockets located on said at least one body or on at least one of said plurality of shelves, said a plurality of electrical sockets adapted to supply electric power;
    at least one carrying mechanism cooperative with said at least one body and adapted to move said plurality of shelves toward the patient; and
    at least one medicine cabinet mounted onto said at least one body, said at least one medicine cabinet adapted to store medicines or serums.

2. The apparatus of claim 1, further comprising:
    a patient tracking application cooperative with said at least one patient tracking monitor.

3. The apparatus of claim 2, wherein said patient tracking application comprises:
    at least one identifying part for receiving an identity number of the patient;
    at least one file number part for receiving a file number of the patient;
    at least one diagnosis selection part for selecting a diagnosis for the patient;

at least one first name-surname part for receiving a first name and a surname of the patient;

at least one warning message part for reminding when a medicine is to be given to the patient;

at least one blood group part when a blood group of the patient is entered;

at least one age part for receiving an age of the patient;

at least one weight part for receiving a weight of the patient;

at least one medical operations part for selecting medical operations and medicines to be given to the patient;

at least one operation part for showing a most recent medical operation or medicine for the patient as selected from the at least one medical operations part;

at least one physician-nurse part for receiving details pertaining to the physician or nurse;

at least one special notes part for receiving notes pertaining to the patient; and at least one report reproduction part for automatically producing reports identifying interventions to the patient and emergency check-in and check-out dates and times.

4. A patient treatment and reporting method for use with emergency services, the patient treatment and reporting method comprising:

placing a plurality of medical devices onto a shelf;

aspirating fluid from the patient;

measuring oxygen levels of the patient;

feeding oxygen to the patient by an oxygen flow meter when the measured oxygen level is low;

respirating medicine to the patient by atomizing fluid with a nebulizer when medicine is required by the patient;

determining a respiration of the patient;

applying a respirator to the patient if the determined respiration is non-existent;

determining a temperature of the patient;

heating the patient with a heater if the determined temperature is too low;

tracking a heart rate and a blood pressure and an oxygen level of the patient with a bedside monitor;

illuminating an area around the patient with an operation lamp;

hanging a serum bag;

supplying electrical power for the medical device from an electrical socket;

retaining narcotic drugs and materials in a password-protected cooling cabinet;

retaining drugs and serums in a medicine compartment;

examining x-ray, MRI or tomography results by a patient survey monitor; and obtaining medical intervention information pertaining to patient and patient information and healthcare personnel detains and repotting by a patient tracking application in a patient tracking monitor.

5. The patient treatment and reporting method of claim 4, wherein the step of obtaining medical intervention information comprising:

creating a new log in the patient tracking application by a sensor;

entering a patient emergency service check-in date and time from the patient tracking application;

obtaining patient details automatically from birth administration records by use of an entered identity number or entering a name and surname of the patient into first name-surname part and an age of the patient into an age part of the patient tracking application;

getting a patient file number from the hospital information management system or by manually entering the patient file number in a file number part of the patient tracking application;

measuring a weight of the patient by the sensor;

entering the measured weight into the weight part of the patient tracking application;

obtaining a blood group of the patient from the hospital information management system or manually entering the blood group into a blood group part of the patient tracking application;

selecting given medicines and applied medical operation to the patient from a medical operation part of the patient tracking application;

reminding a healthcare staff of medicines required by the patient in a reminding massage part of the patient tracking application;

displaying a most recent operation of the patient in a latest operation part of the patient tracking application;

entering a diagnostic decision made from the patient after treatment into a diagnosis selection part of the patient tracking application;

recording a name of the healthcare staff interviewing with the patient in a physician-nurse part of the patient tracking application;

entering notes of the physician into a special notes part of the patient tracking application; and using a report reproduction part of the patient tracking application for issuance of a report after completion of treatment of the patient.

* * * * *